United States Patent [19]

Nishimura et al.

[11] 4,229,589

[45] Oct. 21, 1980

[54] PROCESS FOR PREPARING A DIESTER OF OXALIC ACID

[75] Inventors: Kenji Nishimura; Shinichiro Uchiumi; Kozo Fujii; Keigo Nishihira; Masayoshi Yamashita, all of Ube; Hiroshi Itatani, Ichihara, all of Japan

[73] Assignee: UBE Industries, Ltd., Ube, Japan

[21] Appl. No.: 938,343

[22] Filed: Aug. 31, 1978

[30] Foreign Application Priority Data

Sep. 7, 1977 [JP] Japan ............................. 52/106790

[51] Int. Cl.$^3$ ...................... C07C 67/36; C07C 69/36
[52] U.S. Cl. .................................. 560/193; 560/190; 560/198; 560/204
[58] Field of Search ............... 560/204, 198, 193, 190

[56] References Cited

U.S. PATENT DOCUMENTS 4,041,068  8/1977  Zehner et al. ..................... 560/204
4,138,587  2/1979  Yamasaki et al. .................. 560/204

FOREIGN PATENT DOCUMENTS 2733730  2/1978  Fed. Rep. of Germany .
50-157311 12/1975  Japan .

OTHER PUBLICATIONS

Karrer, Organic Chemistry, p. 100, (1938).

*Primary Examiner*—Jane S. Myers
*Attorney, Agent, or Firm*—Frishauf, Holtz, Goodman & Woodward

[57] ABSTRACT

A process for preparing a diester of oxalic acid which comprises bringing carbon monoxide into contact with an ester of nitrous acid in the liquid phase, in the presence of metallic palladium or a salt thereof, preferably with introduction of a gas containing molecular oxygen into the reaction system, more preferably with further incorporation of an alcohol in the reaction system.

6 Claims, No Drawings

PROCESS FOR PREPARING A DIESTER OF OXALIC ACID

This invention relates to a process for preparing a diester of oxalic acid. More particularly, this invention relates to a process for preparing a diester of oxalic acid by bringing carbon monoxide into contact with an ester of nitrous acid in the liquid phase in the presence of metallic palladium or a salt thereof.

Diesters of oxalic acid have been used as important starting materials for the syntheses of oxalic acid, oxamide, glycols, intermediates for dyes, pharmaceuticals and so on.

There have hitherto been proposed various catalytic systems as illustrated hereinafter with examples for preparing a diester of oxalic acid by bringing an alcohol into contact with carbon monoxide or with carbon monoxide and molecular oxygen under pressure in the liquid phase.

U.S. Pat. No. 3,393,136 has disclosed a catalyst system which comprises a platinum group metal and a soluble copper salt or a soluble iron salt. However, the process has a drawback in that the reaction system must be kept substantially anhydrous and hence a large amount of an expensive dehydrating agent must be used for the purpose. In German Provisional Patent Publication (Offenlegungsschrift) No. 2213435, there has been disclosed a catalyst system which comprises a salt or complex salt of a platinum group metal and a salt or complex salt of a metal which is more electropositive than the platinum group metal. However, the catalyst system also has a defect in that the catalyst is deactivated in a short time and corrosion of the apparatus can not be avoided. Further, U.S. Pat. Nos. 4,005,128 and 4,005,129 have disclosed a catalytic system which comprises a salt of palladium, rhodium, platinum or copper; an amine or ammonia; and a metal oxidant of a salt of copper or iron. In the process, however, there is a drawback in that at least an equivalent amount of a metal oxidant is required for the desired diester of oxalic acid, and hence the recovery and regeneration of the oxidant becomes complicated.

As seen above, all of the conventional processes for preparing a diester of oxalic acid by oxycarbonylation of an alcohol have various defects and have not been applied practically.

In view of the actual circumstances, the present inventors have carried out extensive studies aiming at the establishment of a process for preparing a diester of oxalic acid which is excellent industrially. As the result, the present inventors have found that various defects in the oxycarbonylations of an alcohol which have hitherto been proposed may be improved and a diester of oxalic acid can efficiently be produced industrially when carbon monoxide is contacted with an ester of nitrous acid in the liquid phase in the presence of metallic palladium or a salt thereof, or metallic palladium or a salt thereof and an alcohol with optional introduction of a gas containing molecular oxygen, and accomplished the present invention.

There are many advantageous points in the present process, namely, (i) there is neither trouble of corrosion of the apparatus nor fear of formation of side-products;
(ii) a diester of oxalic acid can be synthesized in high selectivity and in high space time yield even under mild reaction conditions of relatively low temperature and pressure;
(iii) the life of the catalyst is long;
(iv) there is no need for setting expensive apparatus for the recovery and regeneration of auxiliary agents for the reaction; and so on.

According to the process of this invention, when carbon monoxide is contacted with an ester of nitrous acid in the liquid phase in the presence of metallic palladium or a salt thereof, or metallic palladium or a salt thereof and an alcohol, the ester of nitrous acid is consumed to produce a diester of oxalic acid and concomitantly nitrogen monoxide, in an amount which is almost equivalent to the consumed ester of nitrous acid, is generated. In this case, an alcohol need not necessarily be employed, but the reaction proceeds more smoothly and rapidly in case of the presence of an alcohol. Further, in cases where a gas containing molecular oxygen is introduced into the reaction system for contact with the reactants in the presence of metallic palladium or a salt thereof, the reaction is additionally accelerated as compared with the case where a gas containing molecular oxygen is not introduced. Furthermore, when a gas containing molecular oxygen is introduced to be contacted with the reactants in the presence of metallic palladium or a salt thereof and an alcohol, the reaction is further accelerated and the ester of nitrous acid seems not to be consumed in appearance.

The catalyst used for the process of this invention comprises metallic palladium or a salt thereof, for which may be exemplified metallic palladium, its nitrate, sulfate, phosphate, halide, an organic acid salt such as acetate, oxalate, benzoate, etc., and the like. There may also be used a palladium complex salt for the purpose. As the ligand for the complex, there may be mentioned, for example, an alkylphosphine such as trimethylphosphine; and arylphosphine such as triphenylphosphine; an alkylarylphosphine such as diethylphenylphosphine; and triphenyl phosphite. Further, the catalyst may be a complex having =CO, —NO, —CN, halogen or the like as a ligand. It is industrially advantageous to use the catalyst, particularly metallic palladium, which is carried on an inert carrier such as, for example, active carbon, alumina, silica, diatomaceous earth, pumice, zeolite, molecular sieve and so on. Palladium to be used need not necessarily be pure and a noble metal containing palladium as a main component may also be used. The amount of palladium to be used is in the range of 0.1 to $2.0 \times 10^4$ ppm calculated on metallic palladium against the weight of the reaction mixture and it is usually sufficient to use it in an amount of 10 to 200 ppm.

The ester of nitrous acid which is used for the process of this invention may preferably be an ester of nitrous acid with an alcohol having 1 to 20 carbon atoms which alcohol is selected from the group consisting of a saturated mono- and dihydric aliphatic alcohols, an alicyclic alcohol and an aralkyl alcohol. As the preferable alcohols may concretely be mentioned, for example, monohydric aliphatic alcohol such as methanol, ethanol, n-propanol, isopropanol, n-butanol, isobutanol, sec-butanol, tert-butanol, amyl alcohol, hexanol, octanol, lauryl alcohol, cetyl alcohol, etc.; an alicyclic alcohol such as cyclohexanol, methylcyclohexanol, etc.; an aralkyl alcohol such as benzyl alcohol, α-phenethyl alcohol, β-phenethyl alcohol, etc.; and a dihydric aliphatic alcohol such as ethylene glycol, propylene glycol, 1,4-butanediol, 1,6-hexanediol, etc.

These alcohols may contain therein a substituent such as an alkoxyl group which does not inhibit the reaction.

While the amount of the ester of nitrous acid to be used can be changed over a wide range, it is necessary that the reaction system contain at least 2% by weight of the ester based on the reaction medium in order to obtain a satisfactory reaction rate. The higher the concentration of the ester of nitrous acid is, the more speedily the reaction proceeds. Accordingly, the ester of nitrous acid may preferably be used in a concentration of not less than 10% by weight based on the reaction medium. The upper limit of its concentration may be selected optionally so as to obtain the desired reaction rate.

The carbon monoxide which is used in the process of this invention may be pure or may be diluted with an inert gas such as nitrogen, or may contain a small amount of hydrogen or methane gas.

With respect to the partial pressure of carbon monoxide in the reaction system, the higher it is, the higher the reaction rate becomes and the selectivity to the desired product also increases. However, even under relatively low partial pressure thereof, the desired product can be obtained in a satisfactory space time yield and selectivity by admixing a high concentration of the ester of nitrous acid in the reaction system. Usually, the partial pressure of carbon monoxide may preferably be in the range of 5 to 200 atm.

The alcohol which is used together with metallic palladium or a salt thereof for carring out the reaction in the process of this invention is selected from the alcohols which form the above-mentioned ester of nitrous acid. In this regard, the alcohol to be used need not have the same alcohol residue as that in the ester of nitrous acid. However, since transesterification occurs rapidly between the ester of nitrous acid and the alcohol at the time of reaction, it usually is advantageous in view of the procedure to use an alcohol which has the same alcohol residue as that of the ester of nitrous acid. Thus, the reaction rate can be increased further by admixing an alcohol in the reaction system. However, since too much alcohol increases the yield of a diester of carbonic acid which is a side-product, it is desirable to select the concentration of the alcohol to be used so that it may be not more than 50% by weight based on the reaction medium. However, since the alcohol acts as a solvent in addition to a reactant, it may be used up to an amount of around 20 times by volume against the ester of nitrous acid in cases where another solvent is not used or the diester of oxalic acid to be produced has a high melting point and will possibly precipitate.

When a gas containing molecular oxygen is introduced into the system in the process of this invention, it is usually advantageous to introduce carbon monoxide and molecular oxygen from the same inlet or from separate inlets, at the same time or in portions, into the reaction system. However, molecular oxygen need not necessarily be introduced together with carbon monoxide into the reaction system. If desired, carbon monoxide may firstly be reacted with an ester of nitrous acid and a gas containing molecular oxygen may subsequently be introduced in the following step of procedure. A gas containing molecular oxygen may be diluted with an inert gas such as nitrogen and the like, and even with air. When such a gas containing molecular oxygen is introduced into the reaction system, the partial pressure of oxygen is set up taking the explosion limit into consideration and usually is adjusted so that the concentration of oxygen in the gaseous mixture may be not more than 8% by volume.

The reaction may be carried out without any solvent or in a solvent which is inert to the reaction. In cases where the desired product, a diester of oxalic acid, shows high melting point and tends to crystallize, it is advantageous to carry out the reaction in the homogeneous liquid phase by using a solvent. As the suitable solvents may be used for example an ester of a lower aliphatic acid such as ethyl acetate, propyl acetate, butyl acetate, amyl acetate, ethyl propionate, butyl propionate methyl butyrate, ethyl butyrate, propyl butyrate, butyl butyrate, etc.; a diester of an aliphatic dicarboxylic acid such as dimethyl oxalate, diethyl oxalate, dipropyl oxalate, dibutyl oxalate, dimethyl succinate, diethyl succinate, dimethyl adipate, etc.; a diester of carbonic acid such as dimethyl carbonate, diethyl carbonate, dipropyl carbonate, dibutyl carbonate, etc.; an ester of an aromatic carboxylic acid such as methyl benzoate, ethyl benzoate, dimethyl phthalate, etc.; an ether such as dioxane, dibutyl ether, etc.; a hydrocarbon such as benzene, toluene, xylene, cyclohexane, n-hexane, etc.; and other solvents such as monochlorobenzene, dichlorobenzene, nitrobenzene, acetophenone, an alkylsulfone, and alkylsulfoxide, etc.

In cases where the desired diester of oxalic acid is a low-melting liquid, it is industrially advantageous to recycle and use a part of the reaction product as a solvent.

When the process of this invention is practiced by using a relatively high concentration of an ester of nitrous acid, the reaction proceeds at a sufficiently high rate even at a low temperature, and the lower the reaction temperature is, the less side-products are produced. Accordingly, it is advantageous to carry out the reaction at a relatively low temperature while maintaining a desired space time yield by using a high concentration of an ester of nitrous acid. Preferable reaction temperature usually ranges between 20° and 150° C. The process according to this invention may be practiced batchwise or with a continuous system. A continuous system is industrially advantageous since the reaction heat is readily removed in a continuous system as compared with a batchwise system.

The present invention will be explained in more detail by the following non-limiting Examples.

EXAMPLE 1

Into a 300 ml. autoclave were introduced 0.2 g. of a powdery catalyst in which 2% of Pd was carried on an active carbon, 30 g. (256 mmol.) of n-butyl nitrite, 10 g. of n-butanol and 60 g. of di-n-butyl oxalate as a solvent. After carbon monoxide was pressed up to 60 Kg/cm$^2$.G (gauge) into the autoclave, the mixture was heated up to 90° C. with stirring at 500 rpm and then subjected to reaction for 30 minutes. After completion of the reaction, the resulting reaction mixture was cooled and analysed by gas chromatography with respect to the products, whereby 32.6 mmol. of di-n-butyl oxalate, 1.7 mmol. of di-n-butyl carbonate were found to be formed and only 0.3 mmol. of butyraldehyde dibutyl acetal (hereinafter referred to "butyral") was detected as the other side-product. Accordingly, the selectivity to di-n-butyl oxalate was 94.6%. The amount of n-butyl nitrite consumed in the reaction was 68.8 mmol. (corresponding to 2.1 times the mole number of the produced di-n-butyl oxalate), and 44.4 mmol. of NO (nitrogen monoxide), 11.4 mmol. of NO$_2$ (nitrogen dioxide) and 1.3 mmol. of $N_2O$ dinitrogen monoxide) were detected in the gaseous phase.

EXAMPLE 2

Into a 300 ml. autoclave were introduced 0.1 g. of a 10%-Pd-on-carbon (10% -Pd/carbon) powder catalyst, 40 ml. (331.5 mmol.) of n-butyl nitrite and 60 ml. of monochlorobenzene as a solvent. After replacement of the air in the autoclave with nitrogen, carbon monoxide (CO) was pressed into the autoclave up to 60 $Kg/cm^2.G$. The mixture was heated up to 90° C. with stirring at 500 rpm and subjected to reaction for 1 hour. After cooling, the resulting reaction mixture was analyzed by gas chromatography. It was revealed that 12.4 mmol. of di-n-butyl oxalate, 1.1 mmol. of di-n-butyl carbonate, 0.3 mmol. of n-butyraldehyde and 0.3 mmol. of butyral were formed. Accordingly, the selectivity to di-n-butyl oxalate was 89.9%.

The same procedure was repeated except that 5 $Kg/cm^2$. of oxygen ($O_2$) was pressed after heating up to 90° C. As a result, it was found that the reaction was accelerated to a greater extent than when $O_2$ was not used, 21.8 mmol. of di-n-butyl oxalate was produced and 1.1 mmol. of di-n-butyl carbonate was formed as a side product. Accordingly, the selectivity to di-n-butyl oxalate was 95.2%.

EXAMPLE 3

Into a 500 ml. autoclave were introduced 0.2 g. of a 2%-Pd/carbon powder catalyst, 10 ml. (82.9 mmol.) of n-butyl nitrite, 50 ml. of n-butanol and 50 ml. of di-n-butyl oxalate as a solvent. After 60 $Kg/cm^2.G$ of carbon monoxide was pressed thereinto and the temperature was raised up to 70° C. with stirring at 500 rpm, 4 $Kg/cm^2$. of $O_2$ was pressed into the reaction system and the reaction was carried out for 30 minutes. After subsequent cooling, the reaction mixture was analyzed by gas chromatography. As the result, it was revealed that 70.1 mmol. of di-n-butyl oxalate, 2.6 mmol. of di-n-butyl carbonate and 0.6 mmol. of butyral were formed. Accordingly, the selectivity to di-n-butyl oxalate was 96.0%. The amount of n-butyl nitrite after reaction was the same within analytical error as that which had existed before reaction.

EXAMPLE 4

In 100 ml. of n-butanol was suspended 0.1 g. of a 2%-Pd/carbon powder and 1 ml. (corresponding to 0.02 mg of Pd) of the thus obtained suspension was introduced into a 300 ml. autoclave together with 100 ml. of n-butanol and 5 ml. (41.2 mmol.) of n-butyl nitrite. After 60 $Kg/cm^2.G$ of CO was pressed thereinto and the temperature was raised up to 110° C. with stirring, 4 $Kg/cm^2$. of $O_2$ was pressed to carry out the reaction for 2 hours. Subsequently, the reaction mixture was cooled and then analyzed by gas chromatography. It was revealed that 10.1 mmol. of di-n-butyl oxalate, 0.2 mmol. of di-n-butyl carbonate and 0.2 mmol. of butyral were formed.

EXAMPLE 5

Into a pressure-resistant tubular reactor having a nozzle for two kind of fluid at the bottom thereof and having the inside diameter of 20 mm. and the capacity of 100 ml. were charged a feed-solution which had been obtained by suspending 1 g. of a 10%-Pd/carbon powder catalyst per 1 l. of a solution consisting of 70% by weight of n-butyl nitrite and 30% by weight of n-butanol, at the flow rate of 460 g./hr. from the nozzle. At the same time were pressed thereinto a CO gas containing 2.45% by volume of oxygen from the gas inlet of the same nozzle at the flow rate of 3.2 Nl./min. to carry out the reaction by a flow method. The temperature and the total pressure were maintained at 35° C. and 67 $Kg/cm^2.G$, respectively. The liquid and gas discharged from the top of the reactor were cooled and then introduced into a reservoir to separate the liquid from the gas and the reaction liquid was taken out continuously. As a result of an analysis by gas chromatography, it was found that the space time yield of di-n-butyl oxalate was 107 g./l.hr. and the selectivities to di-n-butyl oxalate and butyral were 98.3% and 1.7% respectively based on the amount of n-butanol consumed. The selectivity to di-n-butyl oxalate based on CO was 86.6% and the loss of n-butyl nitrite was 2.7%.

EXAMPLE 6

Using the same reactor as in Example 5, a feed-solution having the same composition as in Example 5 was fed from the bottom at a flow rate of 500 g./hr. At the same time, a CO gas containing 1.97% by volume of $O_2$ was pressed thereinto at a flow rate of 3.2 Nl./min. The reaction temperature and the total pressure were maintained at 51° C. and 67 $Kg/cm^2.G$, respectively.

As a result of gas-chromatographic analysis of the reaction mixture discharged from the top of the reactor, it was revealed that the space time yield of di-n-butyl oxalate was 221 g./l.hr. and the selectivities to di-n-butyl oxalate and butyral were 98.5% and 1.5% respectively based on n-butanol. The selectivity to di-n-butyl oxalate based on CO was 78.3% and the loss of n-butyl nitrite was not more than 1%.

EXAMPLE 7

Into the reactor used in Example 5 were fed a suspension which was obtained by suspending a 10%-Pd/carbon powder so as to be 113 ppm calculated on Pd in a solution consisting of 10.4% by weight of n-butyl nitrite, 41.0% by weight of n-butanol and 48.6% by weight of di-n-butyl adipate (solvent), at a flow rate of 7 l./hr. At the same time, a CO gas containing no $O_2$ was pressed thereinto at a rate of 3.2 Nl./min. The reaction temperature and the total pressure were maintained at 90° C. and 60 $Kg/cm^2.G$, respectively. As a result of gas-chromatographic analysis of the discharged liquid, it was found that the space time yield of di-n-butyl oxalate was 386 g./l.hr. and the selectivities to di-n-butyl oxalate and di-n-butyl carbonate based on n-butanol were 92.9 and 7.1%, respectively. The selectivities to di-n-butyl oxalate, di-n-butyl carbonate and carbon dioxide ($CO_2$) based on CO were 91.2%, 7.1% and 1.8%, respectively.

EXAMPLE 8

Into the reactor used in Example 5 was fed a suspension of a 10%-Pd/carbon powder (amount: corresponding to 105 ppm) in a feed-solution which consists of 9.9% by weight of n-butyl nitrite and 90.1% by weight of di-n-butyl adipate (solvent) and which contains no alcohol, at the flow rate of 500 g./hr. At the same time, a gaseous mixture consisting of 80% by volume of CO and 20% by volume of air was pressed thereinto at a flow rate of 3.2 Nl./min. The reaction temperature and the total pressure were maintained at 90° C. and 70 $Kg/cm^2.G$, respectively. As a result of gas-chromatographic analysis of the discharged liquid, it was found that the space time yield of di-n-butyl oxalate was 69.2 g./l.hr. and any side-product was not detected.

EXAMPLE 9

Into the reactor used in Example 5 was fed the same feed-suspension as in Example 7 at a flow rate of 7 l./hr. At the same time, a gaseous mixture consisting of 5.3% by volume of $O_2$ and 94.7% by volume of CO was pressed into the system at a flow rate of 3.2 Nl./min. The reaction temperature and the total pressure were maintained at 90° C. and 60 Kg./cm$^2$.G, respectively. As a result of gas-chromatographic analysis of the discharged liquid, it was found that the space time yield of di-n-butyl oxalate was 1270 g./l.hr., and the selectivities to di-n-butyl oxalate and di-n-butyl carbonate based on carbon monoxide were 96.7% and 3.3%, respectively. The selectivities based on n-butanol to di-n-butyl oxalate, di-n-butyl carbonate and $CO_2$ were 94.2%, 3.2% and 2.6%, respectively.

EXAMPLE 10

Into the reactor used in Example 5 was introduced a suspension which was prepared by suspending a 10%-Pd/carbon powder (amount: corresponding to 81 ppm calculated on Pd) in a feed-solution consisting of 24.4% by weight of n-butyl nitrite, 21.1% by weight of n-butanol and 54.4% by weight of di-n-butyl adipate as a solvent, at a flow rate of 560 g./hr. At the same time, a gaseous mixture consisting of 88% by volume of CO and 12% by volume of air was pressed into the system at a flow rate of 3.2 Nl./min. The reaction temperature and the total pressure were maintained at 75° C. and 15 Kg/cm$^2$.G, respectively. As a result of gas-chromatographic analysis of the discharged liquid, it was found that the space time yield of di-n-butyl oxalate was 132 g./l.hr., and the selectivities based on n-butanol to di-n-butyl oxalate and di-n-butyl carbonate were 94.1% and 5.9%, respectively.

EXAMPLE 11

An experiment was run in the same manner as in Example 10 except that the reaction was conducted at 90° C. under the reaction pressure of 5 Kg/cm$^2$.G. As the result, it was found that the space time yield of di-n-butyl oxalate was 97 g./l.hr., and the selectivities based on n-butanol to di-n-butyl oxalate and di-n-butyl carbonate were 54.0% and 46.0%, respectively.

EXAMPLE 12

Into the reactor used in Example 5 was introduced a suspension which was obtained by suspending a 10%-Pd/carbon powder so as to be 79 ppm calculated on Pd in a feed-solution consisting of 50.0% by weight of n-butyl nitrite, 35.0% by weight of n-butanol and 15.0% by weight of di-n-butyl adipate as a solvent, at a flow rate of 614 g./hr. At the same time, a gaseous mixture consisting of 89% by volume of CO and 11% by volume of air was pressed into the system at a flow rate of 3.2 Nl./min. The reaction temperature and the total pressure were maintained at 90° C. and 12 Kg./cm$^2$.G, respectively.

As a result of the analysis of the discharged liquid, it was found that the space time yield of di-n-butyl oxalate was 407 g./l.hr., and the selectivities based on n-butanol to di-n-butyl oxalate and di-n-butyl carbonate were 95.1% and 4.9%, respectively.

EXAMPLE 13

Into a 500 ml. autoclave were introduced 0.1 g. of a 2%-Pd/carbon, 40 mmol. of n-butyl nitrite, 70 ml. of n-butanol and 30 ml. of di-n-butyl oxalate (solvent), and 60 Kg/cm$^2$.G of CO gas was pressed thereinto. After the mixture was heated up to 95° C. with stirring, 3 Kg/cm$^2$. of $O_2$ was pressed thereinto and the reaction was carried out for 30 minutes. After cooling, the reaction mixture was analyzed by gas chromatography. As the result, it was found that the output of di-n-butyl oxalate was 35.9 mmol. and the selectivity thereto was 95.4%.

Further, the total amount of the reaction mixture was concentrated under reduced pressure, and n-butyl nitrite and n-butanol were added newly to adjust the liquid composition to the initial one. While the same procedure was repeated 20 times under the same conditions, the deactivation of the catalyst was not observed, and the average selectivity to di-n-butyl oxalate was 97.1%.

EXAMPLES 14 TO 19

Into a 500 ml. autoclave were introduced a predetermined amount of a palladium catalyst, 20 mmol. of n-butyl nitrite and 100 ml. of n-butanol, and 60 Kg/cm$^2$.G of CO was pressed into the system. After the mixture was heated up to 110° C. with stirring, 3 Kg/cm$^2$. of $O_2$ was pressed thereinto and the reaction was carried out for 30 minutes. After subsequent cooling, the reaction mixture was analyzed by gas chromatography. The results are shown in Table 1.

TABLE 1

| | catalyst | | reaction products (mmol.) | | |
|---|---|---|---|---|---|
| Ex. No. | kind | amount (mmol.) | di-n-butyl oxalate | di-n-butyl carbonate | butyral |
| 14 | 2%Pd/silica | 0.038 | 32.9 | 9.1 | 1.6 |
| 15 | 0.5Pd/alumina | 0.038 | 5.7 | 5.7 | 1.7 |
| 16 | PdCl$_2$ | 0.55 | 24.1 | 20.3 | 0.4 |
| 17 | Pd(NO$_3$)$_2$ | 0.038 | 34.6 | 21.0 | 1.7 |
| 18 | PdSO$_4$ . 2H$_2$O | 0.042 | 22.7 | 4.3 | 1.1 |
| 19 | Pd(OAc)$_2$* | 0.038 | 35.7 | 8.6 | 1.1 |

*Palladium Acetate

EXAMPLES 20 TO 29

Into a 500 ml. autoclave were introduced 0.1 g. of a 2%-Pd/carbon powder catalyst, a predetermined amount of each various esters of nitrous acid and a predetermined amount of each various alcohols, and the reaction was conducted at a predetermined temperature and under a predetermined pressure for 30 minutes. After completion of the reaction, each reaction mixture was analyzed by gas chromatography. The results are shown in Table 2.

TABLE 2

| Ex. No. | ester of nitrous acid (amount used: mmol.) | alcohol (amount used: ml.) | reaction pressure (Kg/cm$^2$) CO | $O_2$ | reaction temperature (°C.) | diester of oxalaic acid (output: mmol.) |
|---|---|---|---|---|---|---|
| 20 | ethyl nitrite (20) | ethanol (100) | 60 | 5 | 110 | diethyl oxalate (4.9) |
| 21 | isopropyl | iso- | 60 | 4 | 90 | diiso- |

TABLE 2-continued

| Ex. No. | ester of nitrous acid (amount used: mmol.) | alcohol (amount used: ml.) | reaction pressure (Kg/cm²) CO | reaction pressure (Kg/cm²) O₂ | reaction temperature (°C.) | diester of oxalaic acid (output: mmol.) |
|---|---|---|---|---|---|---|
| | nitrite (40) | propanol (100) | | | | propyl oxalate (39.1) |
| 22 | isobutyl nitrite (40) | iso-butanol (100) | 60 | 4 | 90 | diisobutyl oxalate (45.2) |
| 23 | tert-butyl nitrite (40) | tert-butanol (100) | 60 | 4 | 90 | di-tert-butyl oxalate (3.1) |
| 24 | n-octyl nitrite (40) | n-octanol (100) | 60 | 4 | 90 | di-n-octyl oxalate (23.4) |
| 25 | benzyl nitrite (40) | benzyl alcohol (100) | 60 | 4 | 90 | dibenzyl oxalate (25.3) |
| 26 | 2-methoxyethyl nitrite (30) | methyl-cellosolve (100) | 60 | 4 | 90 | di(2-methoxyethyl) oxalate (17.1) |
| 27 | ester of nitrous acid with ethylene glycol (30) | n-butanol (100) | 53 | 5 | 110 | di-n-butyl oxalate (36.1**) |
| 28 | n-butyl nitrite (40) | cyclohexanol (100) | 60 | 4 | 110 | dicyclohexyl oxalate (10.7) |
| 29 | ester of nitrous acid with ethylene glycol (20*) | ethylene glycol (20*) | 55 | 4 | 90 | di(2-hydroxyethyl) oxalate (4.7) |

*A mixture of 70 ml. of di-n-butyl ether and 50 ml. of dioxane were used as a solvent.
**In addition, 25.9 mmol. of n-butyl nitrite and 10.5 mmol. of di-n-butyl carbonate were also formed.

We claim:

1. A process for preparing a diester of oxalic acid which comprises contacting carbon monoxide with an ester of nitrous acid in the liquid phase in the presence of metallic palladium or a salt thereof under a partial pressure of carbon monoxide of 5 to 200 atm. at a temperature of 20° to 150° C., said ester of nitrous acid being an ester of nitrous acid with an alcohol having 1 to 20 carbon atoms selected from the group consisting of a saturated monohydric aliphatic alcohol, a saturated dihydric aliphatic alcohol, an alicyclic alcohol and an aralkyl alcohol, to produce said diester of oxalic acid containing the same ester group as that of said ester of nitrous acid.

2. A process as claimed in claim 1 wherein a gas containing molecular oxygen is introduced into the reaction system.

3. A process as claimed in claim 1 wherein the amount of said metallic palladium or salt thereof is in the range of 0.1 to $2.0 \times 10^4$ ppm, calculated as metallic palladium, of the reaction mixture.

4. A process as claimed in claim 3 wherein the amount of metallic palladium or salt thereof is in the range of 10 to 200 ppm of the reaction mixture.

5. A process as claimed in claim 1 wherein the concentration of said ester of nitrous acid in the reaction system is at least 2% by weight of the reaction mixture.

6. A process as claimed in claim 2 or claim 1 wherein the reaction mixture also contains an alcohol having 1 to 20 carbon atoms selected from the group consisting of a saturated monohydric aliphatic alcohol, a saturated dihydric aliphatic alcohol, and alicyclic alcohol and an aralkyl alcohol.

* * * * *